United States Patent [19]
Schwartz et al.

[11] Patent Number: 5,769,899
[45] Date of Patent: Jun. 23, 1998

[54] CARTILAGE REPAIR UNIT

[75] Inventors: Robert Elliott Schwartz, Old Westbury; Daniel Anthony Grande, Jr., Seacliff, both of N.Y.

[73] Assignee: Matrix Biotechnologies, Inc., Melville, N.Y.

[21] Appl. No.: 698,468

[22] Filed: Aug. 15, 1996

Related U.S. Application Data

[63] Continuation of Ser. No. 289,387, Aug. 12, 1994, abandoned.

[51] Int. Cl.$^6$ .................................................... A61F 2/30
[52] U.S. Cl. .............................................. 623/18; 623/16
[58] Field of Search ............................... 623/11, 13, 16, 623/18; 606/77, 154, 230; 424/426, 428

[56] References Cited

U.S. PATENT DOCUMENTS

| | | |
|---|---|---|
| 3,745,590 | 7/1973 | Stubstad . |
| 4,055,862 | 11/1977 | Farling . |
| 4,205,400 | 6/1980 | Shen et al. . |
| 4,502,161 | 3/1985 | Wall . |
| 4,604,097 | 8/1986 | Graves, Jr. et al. ........................ 623/11 |
| 4,609,551 | 9/1986 | Caplan et al. .............................. 424/95 |
| 4,627,853 | 12/1986 | Campbell et al. . |
| 4,655,777 | 4/1987 | Dunn et al. ................................ 623/16 |
| 4,796,603 | 1/1989 | Dahlke et al. ............................ 128/899 |
| 4,808,185 | 2/1989 | Penenberg et al. . |
| 4,846,835 | 7/1989 | Grande . |
| 4,880,429 | 11/1989 | Stone . |
| 4,904,259 | 2/1990 | Itay ........................................... 623/16 |
| 4,963,489 | 10/1990 | Naughton et al. . |
| 5,067,964 | 11/1991 | Richmond et al. . |
| 5,084,050 | 1/1992 | Draenart .................................... 606/77 |
| 5,084,051 | 1/1992 | Törmälä et al. .......................... 606/77 |
| 5,123,927 | 6/1992 | Duncan et al. . |
| 5,176,710 | 1/1993 | Hahn et al. . |
| 5,197,985 | 3/1993 | Caplan et al. . |
| 5,263,987 | 11/1993 | Shah . |
| 5,270,300 | 12/1993 | Hunziker ................................... 514/12 |
| 5,306,311 | 4/1994 | Stone et al. ............................... 623/18 |
| 5,360,450 | 11/1994 | Giannini ................................... 623/21 |

FOREIGN PATENT DOCUMENTS

| | | | |
|---|---|---|---|
| 2612392 | 9/1988 | France | .................................... 606/77 |

OTHER PUBLICATIONS

"Surgical Technique For Suretac," Brochure of Acufex Microsurgical (1991).
Pagani, M.J., et al. "Arthroscopic Shoulder Stabilization," Operative Techniques in Sports Medicine, 1, 4 (Cot. 1993) pp,. 276–284.
Stuart, M.J., "Treatment of Chronic Chondral Injuries," Sports Medicine and Arthroscopic Review, 2, 50–58 (1994).
Warner, J.J.P., et al., "Anthroscopic Bankart Repair . . .," Operative Techniques in Orthopaedics, 1, 2 (Apr. 1991), pp. 192–198.
"Bioabsorable . . . from Acufex," 1 page Advertisement (1990).

*Primary Examiner*—Michael J. Milano
*Attorney, Agent, or Firm*—Amster, Rothstein & Ebenstein

[57] ABSTRACT

A bio-absorbable cartilage repair system for regenerating damaged or destroyed articular cartilage on the surface of a bone by establishing a chondrogenic growth-supporting matrix between an area of removed damaged or destroyed articular cartilage and the adjacent healthy cancellous bone. The system is at least one assembly of a bio-absorbable delivery unit, configured and dimensioned to be mounted in both the removed area and the adjacent healthy area, and a porous bio-absorbable insert supported by and in the delivery unit and establishing communication between the removed area and the adjacent healthy area for a chondrogenic growth-supporting matrix. The insert preferably includes a repair factor (e.g., a growth factor, an attachment factor, or both) releasably disposed in the insert to assist in establishing the chondrogenic growth-supporting matrix.

42 Claims, 4 Drawing Sheets

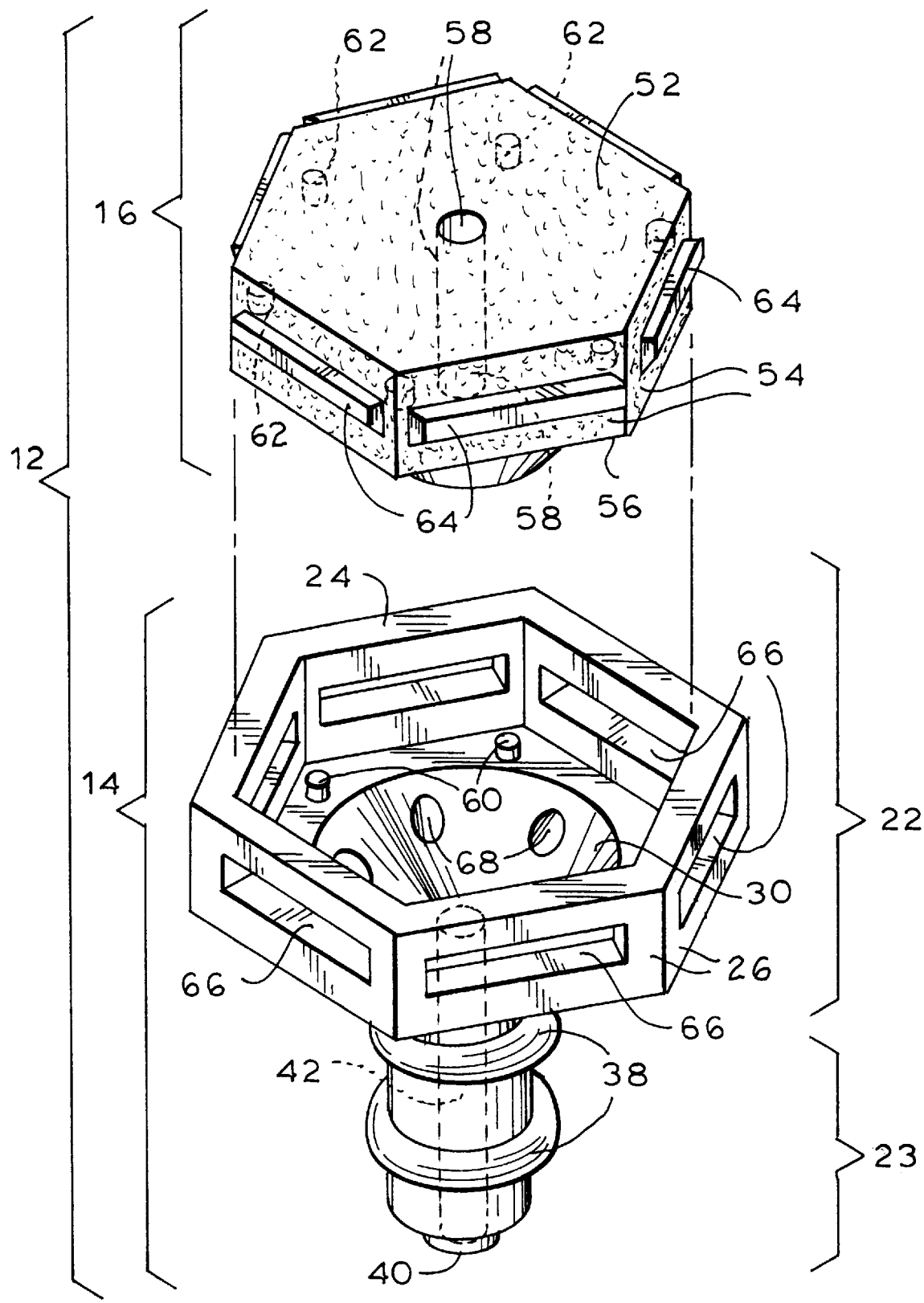
F I G. 2

CARTILAGE REPAIR UNIT

This is a continuation of application Ser. No. 08/289,387 filed on Aug. 12, 1994, now abandoned.

BACKGROUND OF THE INVENTION

This invention relates to a bio-absorbable cartilage repair system for regenerating articular cartilage and, more particularly, a system which allows for vascular invasion and cellular migration between the system and the adjacent healthy area of articular cartilage and cancellous bone, thereby resulting in regeneration of the damaged articular cartilage.

Articular cartilage on the surface of bones in joints, most particularly the knee and hip joints, is susceptible to deterioration caused by injury or disease. This deterioration of cartilage leads to pain and eventually loss of joint movement and severe pain. As a result, various methods have been developed to treat and repair damaged or destroyed articular cartilage.

Prosthetic devices are often used to replace damaged or destroyed articular cartilage. For example, U.S. Pat. No. 4,627,853 discloses prosthesis which are used for articular cartilage replacement. The prosthesis are prepared by demineralization of a bone segment, the demineralized bone segment serving as a replacement for articular cartilage.

U.S. Pat. No. 4,880,429 discloses a prosthetic meniscus which is implanted in the knee. The prosthetic meniscus acts as a scaffold for regrowth of native meniscal tissue, and comprises collagen fibers interspersed with glycoaminoglycan molecules.

U.S. Pat. No. 5,176,710 discloses a prosthesis for replacing bone material on the articulating surface of a joint. The prosthesis has a specific modulus of elasticity so as to confer stiffness to the prosthesis, and contains concave shapes which are suitable for biologic ingrowth.

U.S. Pat. No. 4,502,161 discloses a prosthetic meniscus which replaces the natural meniscus between the articular surfaces of the bones and the joints, and comprises an insert and extension for attachment to the bone and a reinforcing fabric or mesh embedded therein.

U.S. Pat. No. 3,745,590 discloses a prosthesis for the repair or replacement of joints, which prosthesis comprises a body portion, including a stem and ligamentous elements, and allows for tissue ingrowth.

U.S. Pat. No. 5,123,927 discloses a knee prosthesis comprising bone cement containing an antibiotic.

Although there are several prosthetic devices which can be used in the replacement of damaged or destroyed articular cartilage, prosthetic devices have several disadvantages. For example, cements which are used to attach prosthetic devices to bones may loosen and eventually fail. In addition, fragmented cement can move into the joints and associated lymph tissue and cause inflammation and further damage. Further, cements result in the formation of fibrous tissue between the bone and the prosthesis. Another major disadvantage associated with the use of prosthesis is that the prosthetic device may be larger than the damaged cartilage that needs to be replaced, thereby requiring removal of portions of healthy bone and/or cartilage in order to accommodate the prosthetic device. Hence, the need remains for a system for repairing and regenerating articular cartilage which avoids the problems associated with prosthetic devices.

Another means used to treat damaged articular cartilage is the placement of repair pieces onto the bone, which repair pieces substitute for cut-out pieces of cartilage. For example, U.S. Pat. No. 5,067,964 discloses an articular cartilage repair piece which comprises a layer of nonwoven, felted fibrous material which is limp and readily conformable to flat and curved surfaces. The articular cartilage repair piece is attached to the bone, for example, by bio-absorbable screws or pins or like temporary fixation techniques. Fibrous tissue ingrowth eventually surrounds the repair piece, thereby causing the repair piece to be permanently attached to the bone. Although U.S. Pat. No. 5,067,964 discloses an alternative method for repairing damaged articular cartilage, it does not disclose any means or method of regenerating damaged or destroyed articular cartilage. Hence, the need remains for a system for regenerating damaged or destroyed articular cartilage, wherein the regenerated articular cartilage is functionally similar to non-damaged articular cartilage.

Accordingly, an object of this invention is to provide a system for regenerating articular cartilage.

Another object is to provide a system for regenerating articular cartilage wherein the regenerated articular cartilage is functionally superior to fibrous or fibrocartilagenous repairs and is functionally similar to non-damaged articular cartilage.

A further object is to provide a cartilage repair system for use in regenerating damaged or destroyed articular cartilage.

A still further object of the present invention is to provide an embodiment of the cartilage repair system which does employ cement or non-bio-absorbable prosthetic devices.

SUMMARY OF THE INVENTION

It has now been found that the above and related objects of the present invention are obtained by a bio-absorbable cartilage repair system for regenerating damaged or destroyed articular cartilage on the surface of a bone which establishes a chondrogenic growth-supporting matrix between an area of damaged or destroyed articular cartilage that has been removed and the adjacent healthy area of articular cartilage and cancellous or trabecular bone. The system comprises an assembly of a bio-absorbable delivery unit, configured and dimensioned to be mounted in both the removed area and the adjacent healthy area of bone, and a porous bio-absorbable insert, supported by and in the delivery unit and establishing communication between the removed area and the adjacent healthy area for a chondrogenic growth-supporting matrix.

In a preferred embodiment, the insert includes a repair factor releasably disposed in the insert to assist in establishing the chondrogenic growth-supporting matrix. The repair factor may be a growth factor, preferably one selected from the group consisting of fibroblast growth factor, transforming growth factor beta, insulin, insulin-like growth factor, platelet derived growth factor and combinations thereof. Alternatively, the repair factor may be an attachment factor, preferably one selected from the group consisting of fibronectin, RGD polypeptide and combinations thereof. Indeed, the repair factor preferably includes both growth and attachment factors.

The cartilage repair system typically includes a plurality of the aforementioned assemblies, with the delivery units of the assemblies being disposed within the bone and the removed area, and the inserts of the assemblies establishing the chondrogenic growth-supporting matrix over a substantial portion of the removed area. Preferably the delivery units of the assemblies are polygonal in configuration and interfitting.

In another preferred embodiment, the insert consists substantially of a bio-absorbable material selected from the group consisting of hyaluronic acid, polyglycolic acid, collagen, polylactic acid, fibrin clot, periosteal cells, polydioxane, polyester, alginate and combinations thereof, while the delivery unit comprises a bio-absorbable material selected from the group consisting of hyaluronic acid polyglycolic acid, polylactic acid, alginate and combinations thereof. Preferably the delivery unit is integrally molded and defines channels therethrough to allow vascular invasion and cellular migration to an adjacent surface of the insert.

The cartilage repair system preferably includes means precluding relative rotation of the delivery unit and the insert in the delivery unit.

The present invention further encompasses a cartilage repair system adapted to be mounted on the surface of a bone to establish a chondrogenic growth-supporting matrix, wherein the system comprises a bio-absorbable delivery unit configured and dimensioned to be mounted on the bone, the unit including a support frame and means for mounting the unit in the bone, and a porous bio-absorbable insert supported by the support frame to provide a chondrogenic growth-supporting matrix.

In a preferred embodiment, the insert includes a repair factor releasably disposed in the insert to enhance the chondrogenic growth-supporting matrix. Further, the support frame is constructed to allow vascular invasion and cellular migration to the insert. Thus, the support frame preferably has an open top, a bottom defining a plurality of channels therethrough to allow vascular invasion and cellular migration to the bottom of the insert and optionally side walls defining windows through which the insert extends to allow cellular migration to the sides of the insert by an adjacent healthy area of articular cartilage. The unit and the insert define an assembly, and the system preferably consists of a plurality of the assemblies in contiguous and abutting relationship. The unit is preferably more rigid than the insert.

BRIEF DESCRIPTION OF THE DRAWING

The above brief description, as well as further objects, features and advantages of the present invention, will be more fully understood by reference to the following detailed description of the presently preferred, albeit illustrative, embodiments of the present invention when taken in conjunction with the accompanying drawings wherein:

FIG. 2 is an exploded isometric view of one assembly of the cartilage repair system;

DETAILED DESCRIPTION OF THE PREFERRED EMBODIMENTS

Figure 1:
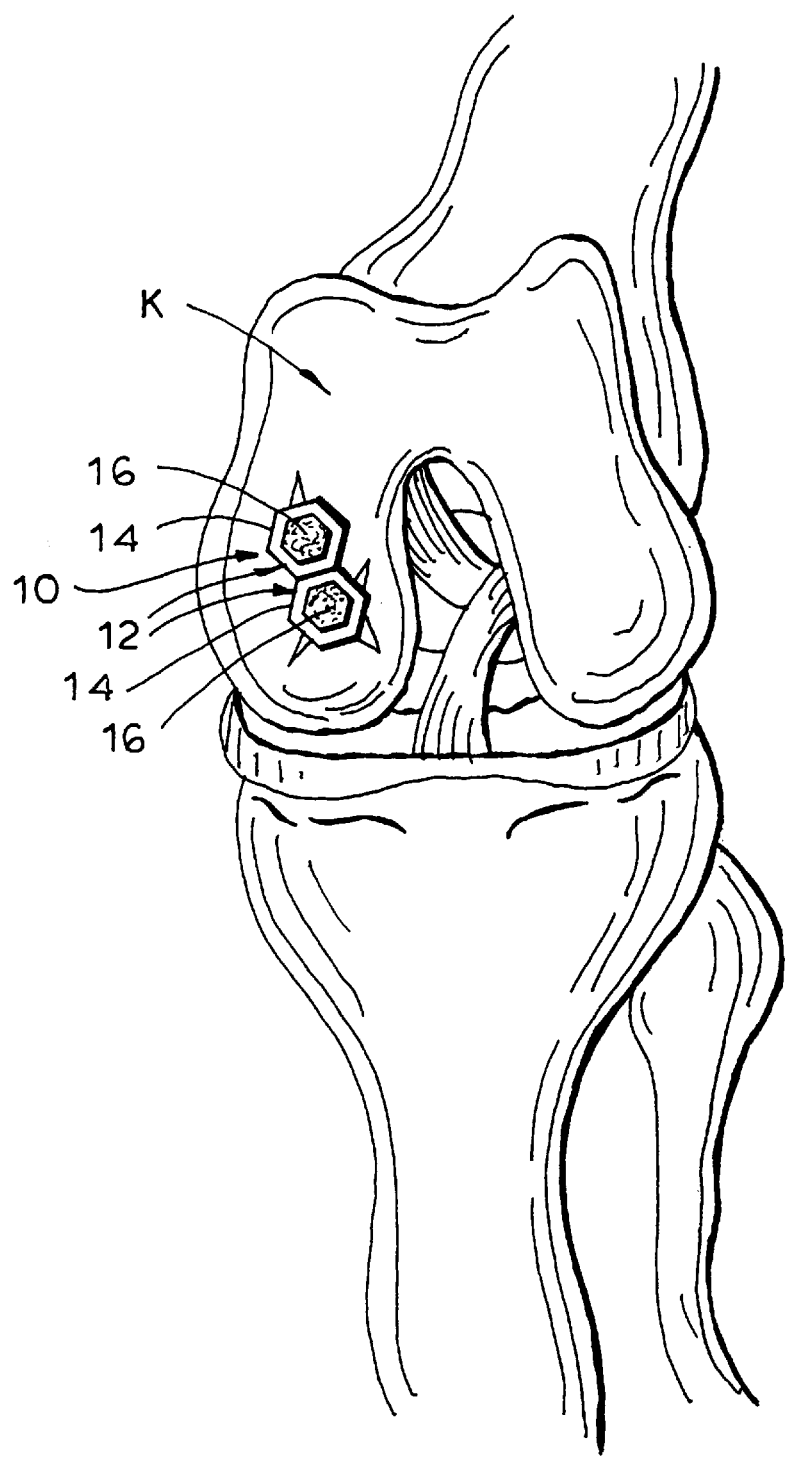
FIG. 1 is a fragmentary schematic view of a knee having therein a pair of assemblies of the cartilage repair system according to the present invention.

Referring now to the drawing, and in particular to FIG. 1 thereof, therein illustrated is a cartilage repair system according to the present invention, generally designated by the reference numeral 10. More particularly, the cartilage repair system 10 illustrated in FIG. 1 is comprised of a plurality of assemblies generally designated 12 (two being illustrated, but it being understood that the requisite number is determined by the extent of the damaged area). Each assembly 12 is in turn comprised of a bio-absorbable delivery unit 14 and a porous bio-absorbable insert 16. The delivery unit 14 is configured and dimensioned to be mounted in both the area from which damaged or destroyed articular cartilage has been removed and the adjacent healthy cancellous bone area of the bone. The porous insert 16 is supported by and in the delivery unit 14 and establishes communication between the removed area (that is, the area from which the damaged or destroyed articular cartilage has been removed) and the adjacent healthy area for a chondrogenic growth-supporting matrix, thereby promoting vascular invasion and cellular migration to achieve articular cartilage regeneration.

Figure 6:
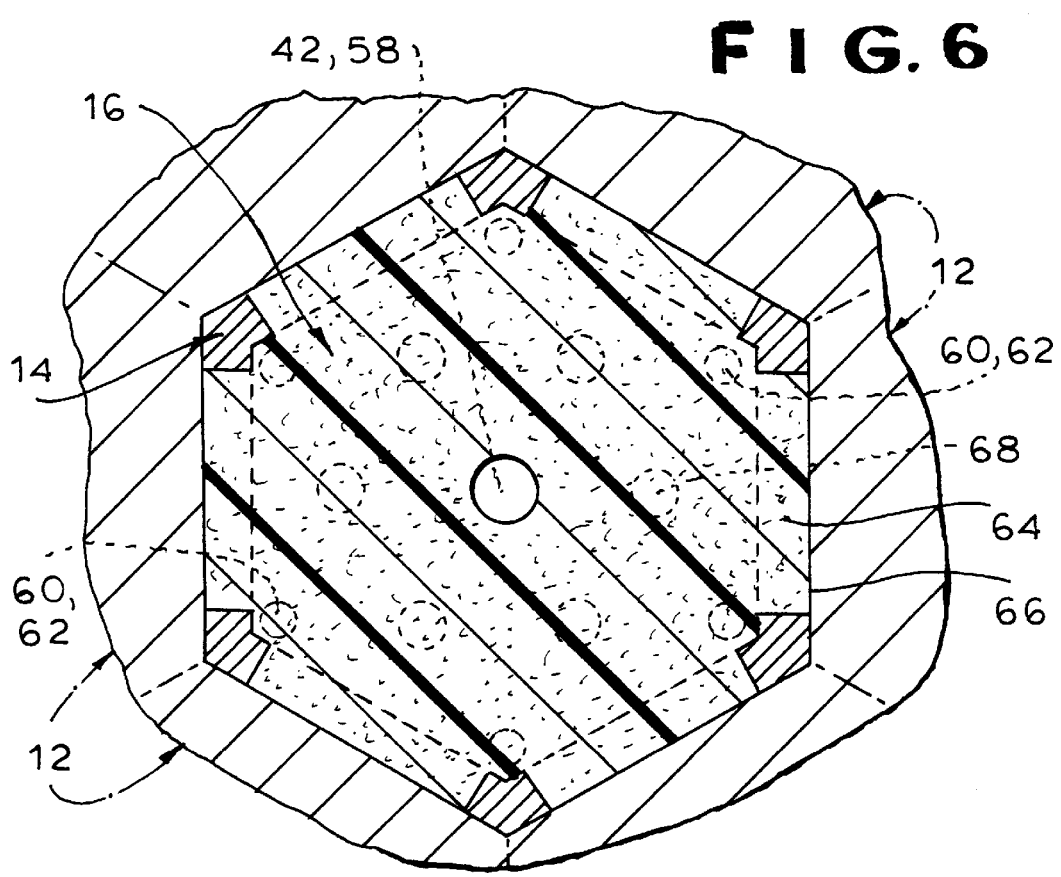
FIG. 6 is a sectional view thereof taken along line 6—6 of FIG. 5, with potential adjacent assemblies being fragmentarily illustrated in phantom line.

While the system 10 is illustrated in FIG. 1 as being used to regenerate damaged or destroyed articular cartilage on the femoral knee joint surface K, those skilled in the medical arts will readily appreciate that the system 10 is equally useful in other articular joints such as the shoulder, hip, and the like. The extent of the damaged or destroyed articular cartilage on the surface of the bone will determine whether the system 10 employs a single assembly 12 or a plurality of assemblies 12. The illustrated assemblies 12 (and in particular the delivery units 14 thereof) are polygonal in plan and interfitting—that is, disposed such that they preferably can be mounted in contiguous abutting contact in a side-to-side relationship. The polygonal nature of the periphery of the assemblies permits interfitting of the assemblies 12 (as generally illustrated in FIG. 6) and is thus preferred where a plurality of the assemblies 12 are to be used to completely cover a designated area of the bone. However, where only a single assembly 12 will be used, other configurations, such as a circular configuration, may be preferred.

While theoretically it might be possible to create in a single manufacturing operation a unitary, one-piece, integral assembly 12 which performs the functions of both the delivery unit 14 and the insert 16, the present invention preferably utilizes two separate and independently formed components—namely, the delivery unit 14 and the insert 16. As will be discussed below in detail, the inserts 16 can be made of a relatively wide variety of different materials and may even include a repair factor (such as a growth factor or an attachment factor) releasably disposed therein to assist in establishing the chondrogenic growth-supporting matrix. Accordingly, the two-component nature of the assembly 12 of the present invention enables the insert 16 to be selected from a supply of different inserts 16 at the time of surgery so as to meet the particular needs of the patient at the time with regard to both the basic composition of the insert 16 and any repair factor composition therein. Again, because of the differing natures of the insert 16 (and any repair factors therein) and its delivery unit 14, it may be necessary for particular types of inserts 16 to be stored before use in different environments from the delivery units 14—for example, in order to provide appropriate preservation of the repair factor. Finally, the delivery unit 14 and insert 16 of an assembly 12 must have different functional characteristics which would be difficult to achieve through known manufacturing techniques in an integral, one-piece, unitary element. Thus, as will be discussed below, the delivery unit 14 must have sufficient strength and integrity to enable it to be tamped into the bone without significant bending or deforming, while the insert 16 is preferably a flexible and resilient porous material in the form of a matrix to enable it to be snapped into the delivery unit 14 and thereby provide a chondrogenic growth-supporting matrix positioned by the delivery unit 14.

Figure 5:
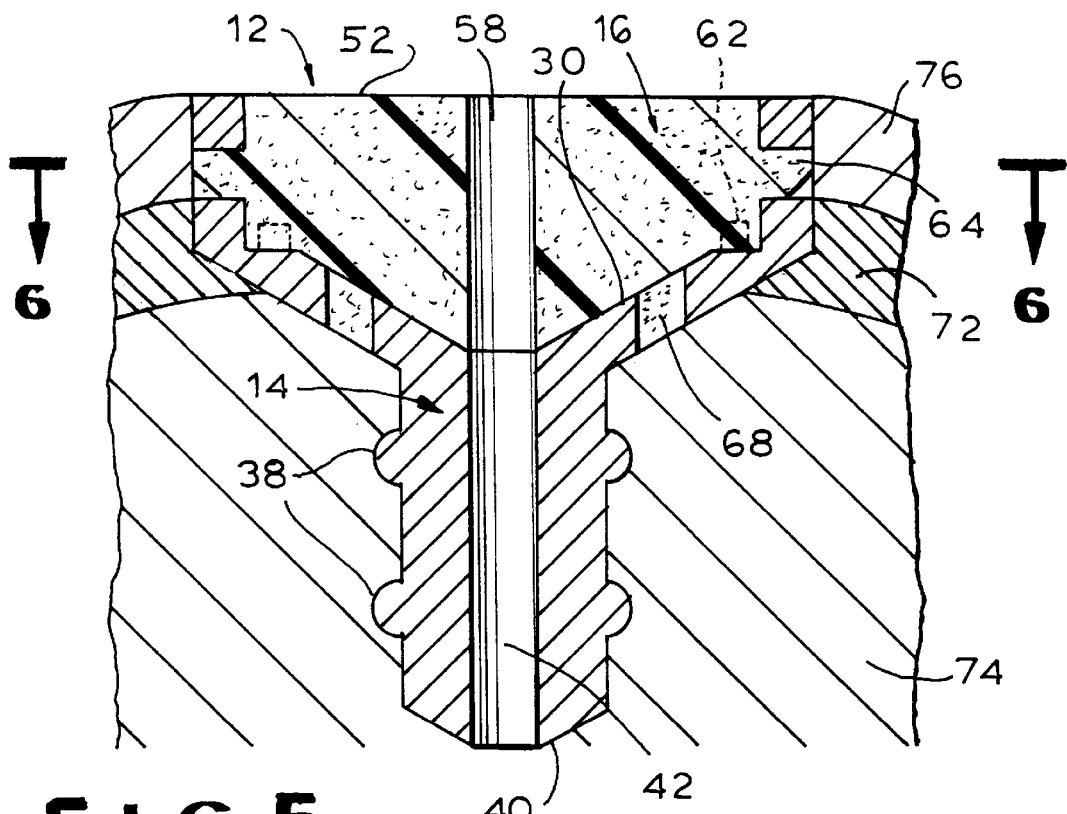
FIG. 5 is a sectional view thereof taken along line 5—5 of FIG. 3 and fragmentarily shows the cartilage repair system inserted into a bone.

Referring specifically to FIGS. 2 and 5, delivery unit 14 is comprised of an upper cup-like support frame 22 and a lower T-like elongate member 23. The support frame 22 has an upper rim 24 defining an open top, side walls 26 and a bottom portion 30. The elongate member 23 (which is preferably cylindrical) extends downwardly from the bottom portion 30 (which is preferably concave) and has radially extending ribs 38, a blunt bevelled bottom 40 and a bore 42 (preferably about 1.5 mm in diameter) extending axially therethrough. The disc- or wafer-like insert 16 has a top surface 52, side walls 54, a bottom surface 56 and a bore 58 (preferably about 1.5 mm in diameter) extending axially therethrough and after insertion into delivery unit 14 coaxial with bore 42 thereof.

The support frame 22 of the delivery unit 14 receives the insert 16 therein, with the side walls 26 of the support frame 22 receiving therewithin the side walls 54 of the insert 50. The bottom surface 56 of the insert 16 and the bottom portion 30 of the support frame 22 are correspondingly shaped, preferably with the bottom surface of the insert 16 defining a protrusion and the upper surface of the bottom portion 30 defining a protrusion-receiving cavity, so that the two bores 42, 58 are automatically and accurately coaxially disposed after the insertion process. In other words, when the insert 16 is secured in the supporting frame 22, the bore 42 through the elongate member 23 and the bore 58 through the insert 16 are in vertically aligned contiguous relationship.

As will readily be appreciated by those skilled in the implant arts, if vascular invasion and cellular migration is to be effected between the healthy cancellous bone area and the area of removed damaged cartilage via the insert 16, means must be provided to preclude relative rotation of the delivery unit 14 and the insert 16. This may be accomplished in a number of different ways.

Figure 3:
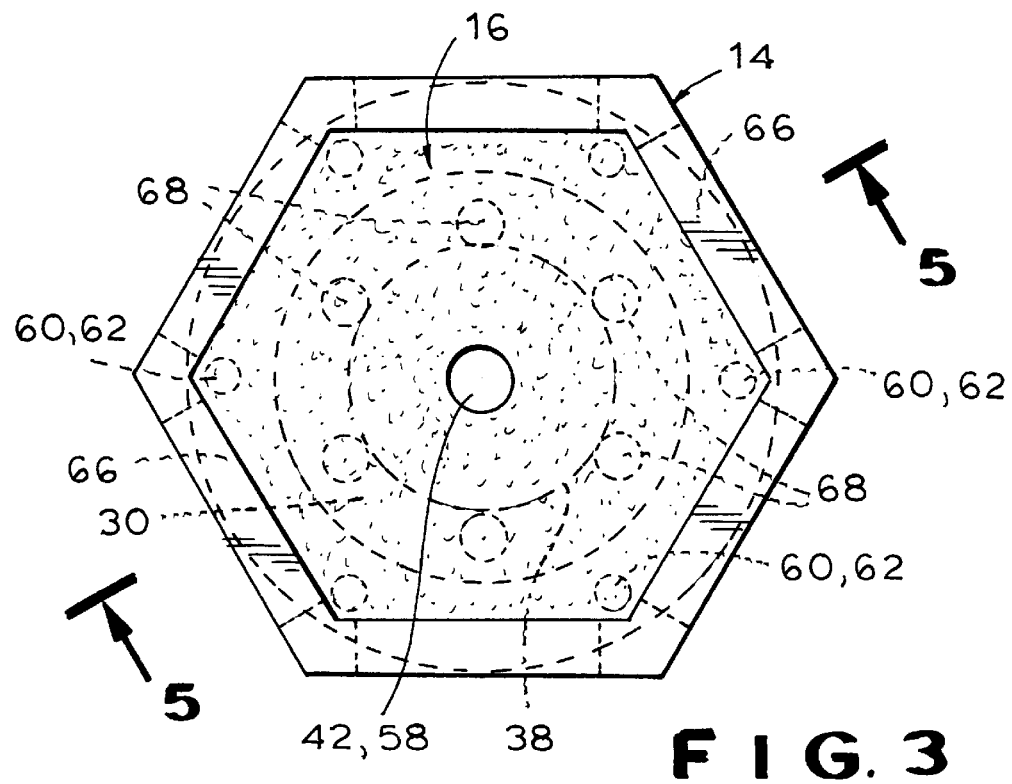
FIG. 3 is a top plan view thereof
Figure 4:
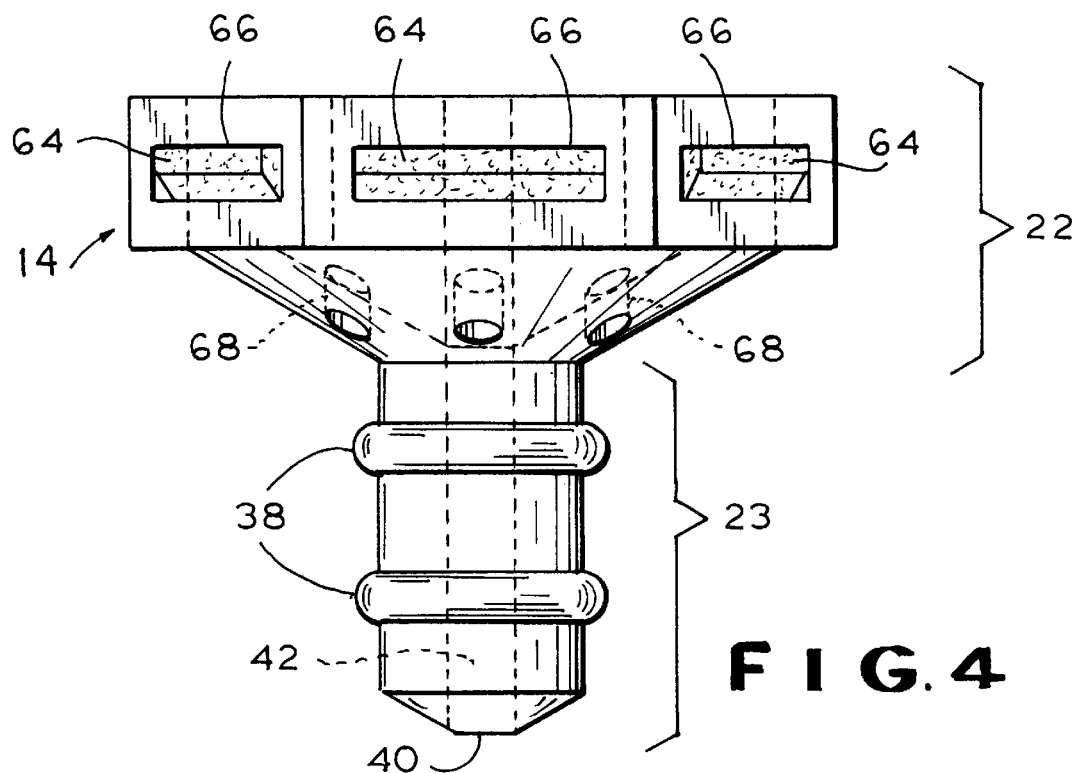
FIG. 4 is a side elevational view thereof.

First, as best seen in FIGS. 2–3 and 6, the external periphery of the insert 16 and the internal periphery of the support frame 22 may be polygonal or irregular (that is, non-circular) and sized to abut one another so that they are locked together for rotation only as a unit. For example, as illustrated, the hexagonal outer periphery of insert 16 snugly fits within hexagonal inner periphery of support frame 22 to preclude relative rotation.

Second, the upper surface of the concave bottom portion 30 of the support frame 22 may define upwardly extending bosses 60 adjacent the side walls 26, while the lower surface of the insert 16 may define upwardly extending recesses 62 configured and dimensioned to receive the bosses 60, as best seen in FIGS. 3 and 6. The number of bosses 60 and recesses 62 as well as the shape, size and placement thereof, are selected so that, when the insert 16 is within the delivery unit 14, the bosses 60 are snugly received in the recesses 62, such that the insert 16 and delivery unit 14 are precluded from relative rotation as long as the insert 16 is within the support frame 22.

Third, the side walls 54 of the insert 16 may define radially outwardly extending flanges 64 therein or therethrough, and the side walls 26 of the support frame 22 may define windows 66 therethrough configured and dimensioned to snugly receive the flanges 64 therein or therethrough. The number of flanges 64 and windows 66, as well as the size, shape and spacing thereof, are selected so that, when the insert 16 is within the support frame 22, relative rotation of the insert 16 and the delivery unit 14 is precluded as long as the flanges 64 snugly extend into (and possibly through) the windows 66. In order to enable the insert 16 with its flanges 64 to be easily inserted into the supporting frame 22 with its windows 66, the insert 16, or at least the flanges 64 thereof, are preferably resiliently flexible. The flanges 64 or windows 66 may also have bevelled edges to facilitate snapping the flanges 64 into the windows 66 during the insertion process.

In the last two alternatives, the height of the bosses 60 and the depth of the recesses 62 or the relative heights of the flanges 64 and windows 66 are selected so that the bottom surface 56 of the insert 16 will rest on the upper surface of the bottom portion 30 of the delivery unit 14. It will be appreciated by those skilled in the mechanical arts that a wide variety of different keying mechanisms well known in the mechanical arts may be used in order to preclude relative rotation of the insert 16 and the delivery unit 14. However, it must be kept in mind that in the present invention, over time, the bio-absorbable elements—that is, the delivery unit 14 and the insert 16—will be disappearing as the human body hydrolyzes the material from which they are made. Accordingly, the selection of an appropriate keying mechanism to preclude relative rotation of the insert 16 and the delivery unit 14 must be made with this consideration in mind. It will be appreciated that while, for the purposes of exposition, a variety of different keying mechanisms have been illustrated in a single embodiment, in fact a single keying mechanism may suffice for a particular embodiment, although a plurality of such mechanisms may also be used.

In order to enable the insert 16 to function as a chondrogenic growth-supporting matrix, it must have access to vascular invasion and cellular migration to regenerate the articular cartilage defect. Such access is provided on the internal periphery of the insert 16 by the bore 58. On the external periphery of the insert 16, the windows 66 on the supporting frame 22 provide direct contact to the adjacent healthy articular cartilage or to the adjacent repair assemblies. These windows 66 allow cellular migration to occur to the insert. The entire top surface 52 of the insert 16 is exposed to the articular environment of the affected joint, and a substantial portion of the bottom surface 56 of the insert 16 is exposed to the cancellous bone through channels 68, which extend axially through the bottom 30 of support frame 22. Providing communication between the area of removed damaged articular cartilage and the healthy cancellous or trabecular bone, the number of the channels 68, as well as the size, shape and placement thereof, is selected to provide a desirable level of communication without unduly deleteriously affecting the strength of the delivery unit 14. The axially disposed channels 68 are, of course, disposed radially outwardly of the elongate member 23 so that the channels 68 do not have to extend axially therethrough.

The delivery unit 14 is hard and preferably does not bend or deform under expected pressures. It is preferably integrally molded. It is critical that the delivery unit 14 be made of a bio-absorbable material such as those well known in the implant art. For example, it is preferably made of polyglycolic acid, polylactic acid or combinations thereof (e.g., copolymers and mixtures thereof) each of the foregoing materials inherently being dimensionally stable against substantial expansion by absorption of synovial joint fluid.

Several delivery units 14 can be placed contiguously in an area of removed damaged articular cartilage such that a large portion of the removed area will be filled with the assemblies 12. In this case, the delivery units 14 are preferably regular polygons and interfitting in an abutting and contiguous relation. A circular delivery unit may be used where only one delivery unit is employed or where only partial coverage of the removed area is desired.

The insert 16 is made substantially of porous material in the form of a matrix or sponge, preferably defining at least 95% voids by volume, so that it can serve as a biological scaffold for an invasion of cells to regenerate the articular cartilage. It typically has the felt-like feel of a non-woven fabric. The insert 16 may be manually bendable or flexible when it is necessary to push, press or snap the same into the delivery unit 14. It is critical that the insert 16 consists substantially (typically at least 99% by weight) of a bio-absorbable material selected from the group consisting of hyaluronic acid (e.g. as a fiber matrix), polyglycolic acid (e.g., as fiber matrix), collagen, including type I collagen (e.g., as a sponge matrix), polylactic acid (e.g. as a fiber matrix), fibrin clot (which can be filled and molded into the delivery unit), collagen gel (which can be overlayed into a polyglycolic acid matrix), isolated periosteal cells, polydioxane, polyester, alginate or combinations thereof. The polylactic acid, and to a lesser degree the hyaluronic acid, polyglycolic acid, and alginate, contribute to the hardness and longevity (i.e., life in situ after implantation) of the insert 16. The insert may be annealed (i.e., heat-treated or cooked) to modify its crystallinity and thus its hardness and longevity. The isolated periosteal cells may be cultured in the insert material or overlaid at the time of surgery into the insert material. Other cell types, such as mesenchymal stem cells or chondrocytes, may also be added to the insert material.

In addition, in a preferred embodiment of the invention, the insert 16 can contain within the matrix "repair factors" such as growth factors and/or attachment factors well known in the medical arts. For example, the insert 16 can contain, as growth factors, fibroblast growth factor (acidic or basic), transforming growth factor-beta (1, 2, 3 or one of the members of the supergene family of TGF-beta, such as bone morphogenic protein; BMP), insulin, insulin-like growth factor 1 & 2, platelet-derived growth factor or combinations thereof. The attachment factors which can be used in the insert include fibronectin, RGD polypeptide and combinations thereof. Typically, the repair factors total less than 1% by weight of the insert, but can range up to 10% depending on the factors' specific activities and release kinetics. The repair factors may be chemically combined with the basic implant composition (e.g., during polymerization thereof) or may be added to an already formed basic implant composition. In the former case, additional repair factor will typically become available as the basic implant composition biodegrades.

Referring now to FIG. 5, after surgical removal of the damaged or destroyed articular cartilage, the elongate member 23 (extending downwardly from the concave bottom portion 30 of the support frame 22) is placed into the cancellous bone 74 through the sub-chondral bone plate 72 which is below of the damaged articular cartilage area. The support frame 22 is supported by the sub-chondral bone plate 72. The elongate member 23 has a blunt bevelled bottom 40 so that the elongate member 23 can be placed easily into the cancellous bone 74, which is a soft region of the bone. The bottom 40 of the elongate cylindrical member 23 is blunt so that the bottom 40 does not break when the elongate cylindrical member 23 is placed inside the cancellous bone 74. When the elongate member 23 is placed into the soft cancellous bone 74, the cancellous bone 74 is displaced by, and reforms around, the radially extending ribs 38 of the elongate member 23. In this manner, the elongate member 23, and thereby the entire cartilage repair system 10, is held in place.

When the delivery unit 20 is placed in the bone, the upper rim 24 of the support frame 22 is planar with undamaged articular cartilage 76. The windows 66 and the upper rim 24 of the support frame 22 are not placed inside the bone, but rather remain exposed to the surrounding articular cartilage. The top surface 52 of the polymer insert 50 is exposed to the joint space environment. The top portion of the exterior surface of the side walls 26 of the support frame 22 laterally abuts either the top portion of the exterior surface of the side walls 26 of adjacent support frames 22 (see FIG. 6), or undamaged articular cartilage 76 when placed adjacent a peripheral portion of an area of removed cartilage. The bottom portion of the exterior surface of the side walls 26 of the support frame 22 (i.e., the portions below windows 66) rests on and laterally abuts the sub-chondral bone plate 72.

When the cartilage repair system of the invention is placed in an area of removed damaged articular cartilage, through the sub-chondral bone plate 72 into the cancellous bone 74, the channels 68 in the bottom portion 30 of the support frame 22 allow for communication between the healthy cancellous bone 74 and the damaged articular cartilage area via a chondrogenic growth-supporting matrix. This permits vascular invasion and cellular migration, which results in regeneration of the articular cartilage. The regenerated articular cartilage is functionally similar to undamaged articular cartilage. The cartilage repair system of the invention is bio-absorbed over time and therefore need not be surgically removed during or after cartilage regeneration. The absorption rate is formula controlled and can range from 6–12 weeks to one year depending on its site-specific application.

As the basic bio-absorbable composition of the insert 16 degrades or hydrolyzes over time, any repair factors contained therein are progressively released into the site, thus further promoting cellular regeneration. Cellular regeneration occurs throughout the insert.

The term "bio-absorbable" is used in the specification and claims hereof to indicate a material which will be degraded or absorbed by the body such that regenerated articular cartilage thereabout is functionally similar to non-damaged articular cartilage.

To summarize, the present invention provides a system for regenerating articular cartilage wherein the regenerated articular cartilage is functionally similar to non-damaged articular cartilage and therefore replaces damaged or destroyed articular cartilage without employing cement or a non-bio-absorbable prosthetic device.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

We claim:

1. A bio-absorbable cartilage repair system for regenerating damaged or destroyed articular cartilage on a joint surface of a bone by establishing a chondrogenic growth-supporting matrix between an area of damaged or destroyed articular cartilage that has been removed and an adjacent healthy area of articular cartilage and subchondral cancellous bone, said system comprising an assembly of:

(A) a delivery unit consisting substantially of completely bio-absorbable material which is dimensionally stable against substantial expansion by absorption of synovial joint fluid and configured and dimensioned to be mounted in both an area of damaged or destroyed articular cartilage that has been removed and an adjacent healthy area of articular cartilage and subchondral cancellous bone; and (B) a porous insert supported by said delivery unit, consisting substantially of completely bio-absorbable material, and defining at least 95% voids by volume for establishing communication between the removed area and the adjacent healthy area for a chondrogenic growth-supporting matrix.

2. The cartilage repair system of claim 1 wherein said insert includes a repair factor releasably disposed in said insert to assist in establishing said chondrogenic growth-supporting matrix.

3. The cartilage repair system of claim 2 wherein said repair factor is a growth factor.

4. The cartilage repair system of claim 3 wherein said growth factor is selected from the group consisting of fibroblast growth factor, transforming growth factor beta, insulin, insulin-like growth factor, platelet-derived growth factor and combinations thereof.

5. The cartilage repair system of claim 2 wherein said repair factor is an attachment factor.

6. The cartilage repair system of claim 5 wherein said attachment factor is selected from the group consisting of fibronectin, RGD polypeptide and combinations thereof. selected from the group consisting of hyaluronic acid, polyglycolic acid, collagen, polylactic acid, fibrin clot, periosteal cells, polydioxane, polyester, alginate and combinations thereof.

7. The cartilage repair system of claim 1 wherein said insert consists substantially of a bio-absorbable material.

8. The cartilage repair system of claim 1 wherein said delivery unit comprises a bio-absorbable material selected from the group consisting of hyaluronic acid, polyglycolic acid, polylactic acid, alginate and combinations thereof.

9. The cartilage repair system of claim 1 wherein said delivery unit defines channels therethrough to allow vascular invasion and cellular migration to an adjacent surface of said insert.

10. The cartilage repair system of claim 1 wherein said delivery unit is integrally molded.

11. The cartilage repair system of claim 1 including means precluding relative rotation of said delivery unit and said insert in said delivery unit.

12. The cartilage repair system of claim 1 wherein said delivery unit defines channels therethrough to allow vascular invasion and cellular migration to an adjacent surface of said insert; and said assembly includes means precluding relative rotation of said delivery unit and said insert in said delivery unit.

13. The cartilage repair system of claim 12 including a plurality of assemblies, said delivery units of said assemblies being disposed within said healthy area of bone and said removed area, and said inserts of said assemblies establishing said chondrogenic growth-supporting matrix over a substantial portion of said removed area, said delivery units of said assemblies being polygonal in configuration and interfitting.

14. The cartilage repair system of claim 12 wherein said insert consists substantially of a bio-absorbable material selected from the group consisting of hyaluronic acid, polyglycolic acid, collagen, polylactic acid, fibrin clot, periosteal cells, polydioxane, polyester, alginate and combinations thereof; and said delivery unit comprises a bio-absorbable material selected from the group consisting of hyaluronic acid, polyglycolic acid, polylactic acid, alginate and combinations thereof.

15. The cartilage repair system of claim 1 wherein said delivery unit is configured as a polygon and dimensioned to be mounted in an area of damaged or destroyed articular cartilage that has been removed and an adjacent healthy area of articular cartilage and cancellous bone.

16. The cartilage repair system of claim 12 wherein said insert includes a repair factor releasably disposed in said insert to assist in establishing said chondrogenic growth-supporting matrix, said repair factor being selected from the group consisting of a growth factor, an attachment factor and combinations thereof.

17. The cartilage repair system of claim 1 wherein said insert includes cells selected from the group consisting of isolated periosteal cells, mesenchymal stem cells, chondrocytes and combinations thereof.

18. A bio-absorbable cartilage repair system for regenerating damaged or destroyed articular cartilage on a joint surface of a bone by establishing a chondrogenic growth-supporting matrix between an area of damaged or destroyed articular cartilage that has been removed and an adjacent healthy area of articular cartilage and subchondral cancellous bone, said system comprising an assembly of:

(A) a delivery unit consisting substantially of completely bio-absorbable material which is dimensionally stable against substantial expansion by absorption of synovial joint fluid and configured and dimensioned to be mounted in both an area of damaged or destroyed articular cartilage that has been removed and an adjacent healthy area of articular cartilage and subchondral cancellous bone; and (B) a porous insert supported by said delivery unit, consisting substantially of completely bio-absorbable material, and defining at least 95% voids by volume for establishing communication between the removed area and the adjacent healthy area for a chondrogenic growth-supporting matrix;

said system including a plurality of assemblies, said delivery units of said assemblies being disposed within said bone and said removed area, and said inserts of said assemblies establishing said chondrogenic growth-supporting matrix over a substantial portion of said removed area.

19. The cartilage repair system of claim 18 wherein said delivery units of said assemblies are polygonal in configuration and interfitting.

20. The cartilage repair system of claim 18 wherein said insert includes cells selected from the group consisting of isolated periosteal cells, mesenchymal stem cells, chondrocytes and combinations thereof.

21. A cartilage repair system adapted to be mounted on a joint surface of a bone to establish a chondrogenic growth-supporting matrix, comprising a delivery unit consisting substantially of completely bio-absorbable material which is dimensionally stable against substantial expansion by absorption of synovial joint fluid and configured and dimensioned to be mounted on and within the bone, said unit including a support frame and means for mounting said unit on and within the bone, and a porous insert consisting substantially of completely bio-absorbable material, defining at least 95% voids by volume, and supported by said support frame to provide a chondrogenic growth-supporting matrix.

22. The cartilage repair system of claim 21 wherein said insert includes a repair factor releasably disposed in said insert to assist in providing said chondrogenic growth-supporting matrix.

23. The cartilage repair system of claim 21 wherein said support frame is constructed to allow vascular invasion and cellular migration to said insert.

24. The cartilage repair system of claim 23 wherein said support frame has an open top and a bottom defining a plurality of channels therethrough to allow vascular invasion and cellular migration to the bottom of said insert.

25. The cartilage repair system of claim 24 wherein said insert has sides, and said support frame has side walls defining windows through which said insert extends to allow cellular migration to the sides of said insert by an adjacent healthy area of articular cartilage.

26. The cartilage repair system of claim 21 wherein said unit and said insert define an assembly, and said system consists of a plurality of said assemblies in contiguous and abutting relationship.

27. The cartilage repair system of claim 21 wherein said unit is more rigid than said insert.

28. The cartilage repair system of claim 21 additionally including means precluding relative rotation of said unit and said insert.

29. The cartilage repair system of claim 21 wherein said insert includes cells selected from the group consisting of isolated periosteal cells, mesenchymal stem cells, chondrocytes and combinations thereof.

30. A bio-absorbable cartilage repair system for regenerating damaged or destroyed articular cartilage on a surface of a bone by establishing a chondrogenic growth-supporting matrix between an area of damaged or destroyed articular cartilage that has been removed and an adjacent healthy area of articular cartilage and cancellous bone, said system comprising an assembly of:
(A) a bio-absorbable delivery unit configured and dimensioned to be mounted in both an area of damaged or destroyed articular cartilage that has been removed and an adjacent healthy area of articular cartilage and cancellous bone; and
(B) a porous, bio-absorbable insert supported by said delivery unit and establishing communication between the removed area and the adjacent healthy area for a chondrogenic growth-supporting matrix;
said delivery unit having an open top, a bottom and a sidewall connecting said top and bottom, said bottom defining a plurality of channels therethrough to allow vascular invasion and cellular migration through the bottom of said insert, and said sidewall defining windows to which said insert extends to allow cellular migration to the sides of said insert by an adjacent healthy area of articular cartilage.

31. A bio-absorbable cartilage repair system for regenerating damaged or destroyed articular cartilage on a joint surface of a bone by establishing a chondrogenic growth-supporting matrix between an area of damaged or destroyed articular cartilage that has been removed and an adjacent healthy area of articular cartilage and subchondral cancellous bone, said system comprising an assembly of:
(A) a delivery unit consisting substantially of completely bio-absorbable material to be mounted in both an area of damaged or destroyed articular cartilage that has been removed and an adjacent healthy area of articular cartilage and subchondral cancellous bone, said delivery unit including means for retaining itself in the adjacent healthy area without either an expansion of the dimensions thereof or a relative rotation thereof; and
(B) a porous insert supported by said delivery unit, consisting substantially of completely bio-absorbable material, and establishing communication between the removed area and the adjacent healthy area for a chondrogenic growth-supporting matrix.

32. The cartilage repair system of claim 31 wherein said delivery unit defines channels therethrough to allow vascular invasion and cellular migration to an adjacent surface of said insert; and
said assembly includes means precluding relative rotation of said delivery unit and said insert in said delivery unit.

33. The cartilage repair system of claim 31 wherein said delivery unit comprises a platform to receive and support said insert and a plug to mount said platform relative to the adjacent healthy area, said plug including said retaining means.

34. The cartilage repair system of claim 32 wherein said insert includes a repair factor releasably disposed in said insert to assist in establishing said chondrogenic growth-supporting matrix, said repair factor being selected from the group consisting of a growth factor, an attachment factor and combinations thereof.

35. The cartilage repair system of claim 31 wherein said insert includes cells selected from the group consisting of isolated periosteal cells, mesenchymal stem cells, chondrocytes and combinations thereof.

36. A cartilage repair system adapted to be mounted on a joint surface of a bone to establish a chondrogenic growth-supporting matrix, comprising a delivery unit consisting substantially of completely bio-absorbable material and configured and dimensioned to be mounted on and within the bone, said delivery unit including a support frame and means for mounting said delivery unit on and within the bone, said delivery unit including means for retaining itself in the bone without either an expansion of the dimensions thereof or a relative rotation thereof, and a porous insert consisting substantially of completely bio-absorbable material and supported by said support frame to provide a chondrogenic growth-supporting matrix.

37. The cartilage repair system of claim 36 wherein said insert includes cells selected from the group consisting of isolated periosteal cells, mesenchymal stem cells, chondrocytes and combinations thereof.

38. A bio-absorbable cartilage repair system for regenerating damaged or destroyed articular cartilage on a joint surface of a bone by establishing a chondrogenic growth-supporting matrix between an area of damaged or destroyed articular cartilage that has been removed and an adjacent healthy area of articular cartilage and subchondral cancellous bone, said system comprising an assembly of:
(A) a bio-absorbable delivery unit configured, as a polygon and dimensioned to be mounted in an area, of damaged or destroyed articular cartilage that has been removed and an adjacent healthy area of articular cartilage and subchondral cancellous bone, said delivery unit including means for retaining itself in the adjacent healthy area without either an expansion of the dimensions thereof or a relative rotation thereof; and
(B) a porous, bio-absorbable insert supported by said delivery unit and establishing communication between the removed area and the adjacent healthy area for a chondrogenic growth-supporting matrix.

39. The cartilage repair system of claim 38 wherein said delivery unit comprises a platform to receive and support said insert and a plug to mount said platform relative to the adjacent healthy area, said plug including said retaining means.

40. The cartilage repair system of claim 38 wherein said insert includes cells selected from the group consisting of isolated periosteal cells, mesenchymal stem cells, chondrocytes and combinations thereof.

41. A bio-absorbable cartilage repair system for regenerating damaged or destroyed articular cartilage on a joint surface of a bone by establishing a chondrogenic growth-supporting matrix between an area of damaged or destroyed articular cartilage that has been removed and an adjacent healthy area of articular cartilage and subchondral cancellous bone, said system comprising an assembly of:

(A) a porous, bio-absorbable insert defining at least 95% voids by volume for establishing communication between a removed area and an adjacent healthy area for a chondrogenic growth-supporting matrix; and (B) a bio-absorbable delivery unit configured and dimensioned to be mounted in the removed area and the adjacent healthy area, said delivery unit including means for positioning said insert in the removed area and surrounded by the adjacent healthy area.

42. The cartilage repair system of claim 41 wherein said insert includes cells selected from the group consisting of isolated periosteal cells, mesenchymal stem cells, chondrocytes and combinations thereof.

* * * * *